United States Patent [19]

Mathew et al.

[11] 4,256,668
[45] Mar. 17, 1981

[54] REMOVING AQUEOUS AMMONIUM SULFATE FROM OXIME PRODUCT

[75] Inventors: Chempolil T. Mathew, Randolph; Donald Pickens, Mendham, both of N.J.

[73] Assignee: Allied Chemical Corporation, Morris Township, Morris County, N.J.

[21] Appl. No.: 50,356

[22] Filed: Jun. 20, 1979

[51] Int. Cl.$^3$ .................. C07C 131/00; C07C 131/04
[52] U.S. Cl. .................................. 564/255; 210/634; 564/264; 564/267; 564/268
[58] Field of Search ............ 260/566 A; 210/22, 23 R

[56] References Cited

U.S. PATENT DOCUMENTS

| | | | |
|---|---|---|---|
| 2,820,825 | 1/1958 | Hillyer et al. | 260/566 A |
| 3,873,624 | 3/1975 | Mathew et al. | 260/601 R |
| 3,921,331 | 1/1976 | Mathew et al. | 260/601 R |
| 3,991,115 | 11/1976 | Purgason | 260/566 A |
| 4,031,139 | 6/1977 | Rapp et al. | 260/566 A |

OTHER PUBLICATIONS

Jordan, George V., "Coalescing of Fluids Through Porous Materials", Bulletin of the Selas Corporation of America (1965).

*Primary Examiner*—Natalie Trousof
*Assistant Examiner*—L. Hendriksen
*Attorney, Agent, or Firm*—Alan M. Doernberg; Jay P. Friedenson

[57] ABSTRACT

An organic, substantially water-insoluble oxime product is recovered from the liquid reaction mixture of water, ammonium sulfate and the oxime product. First the reaction mixture is separated into a first liquid layer containing an aqueous ammonium sulfate solution and a second liquid layer containing an emulsion of the oxime product as the continuous phase and aqueous ammonium sulfate as the discontinuous phase. These layers are separated and the second liquid layer is contacted with solid ammonium sulfate for a time sufficient to agglomerate the discontinuous phase. The agglomerated discontinuous phase is then removed from the continuous phase. Thereafter, either a lites fraction can be distilled from the continuous phase or the oxime product can be distilled from the continuous phase, or both. The process is particularly applicable to the production of oximes such as Aldicarb oxime, cyclohexanone oxime and methylethylketoxime from aqueous reaction mixtures in which by-product ammonium sulfate is formed.

7 Claims, No Drawings

REMOVING AQUEOUS AMMONIUM SULFATE FROM OXIME PRODUCT

DESCRIPTION

BACKGROUND OF THE INVENTION

Ammonium sulfate is produced as a by-product from many processes for producing organic materials. In particular, a common method of producing oximes is to oximate an aldehyde or ketone with aqueous hydroxylamine salts under pH conditions such as 5–8. Exemplary processes are included in U.S. Pat. Nos. 3,873,624 and 3,931,331 to Mathew et al. Frequently, the hydroxylamine salt used is hydroxylamine sulfate, sometimes drawn as $(H_2NOH)_2 \cdot H_2SO_4$ or $(H_3NOH)_2SO_4$ and the pH is raised by using gaseous ammonia. Under such conditions, the product oxime, ammonium sulfate and water are produced. Most oximes are relatively insoluble or immiscible with water such that a phase separation occurs. The bulk of the ammonium sulfate is present in an easily separated first aqueous layer which is removed. Thereafter, the product is purified from the remaining material (the second or organic layer) by one or more distillations such as a lites distillation to remove various by-products and then, unless the product is relatively high boiling, a product distillation to recover the oxime in the overhead.

It has been found that, in spite of the removal of most of the ammonium sulfate as a solution in a separate first layer, sufficient ammonium sulfate remains as an aqueous discontinuous layer in the second layer to complicate later purification techniques. Thus, when the organic material is subjected to lites distillation, particularly if substantial quantities of water are removed by lites distillation, then any ammonium sulfate present in the discontinuous phase can crystallize out of the remaining liquid. These crystals can coat equipment, block filters and other devices and complicate the remaining separation in various ways.

Accordingly, it is an object of this invention to recover the organic, substantially water-insoluble oxime product with a substantially reduced ammonium sulfate content prior to any distillation so as to prevent problems associated with ammonium sulfate crystallization.

BRIEF DESCRIPTION OF THE INVENTION

The present invention includes a process for recovering an organic, substantially water-insoluble oxime product from a liquid reaction mixture comprising water, ammonium sulfate and the product, which process comprises:

(1) separating the reaction mixture into a first liquid layer comprising an aqueous ammonium sulfate solution and a second liquid layer comprising an emulsion of the organic oxime product as the continuous phase and aqueous ammonium sulfate as the discontinuous phase;

(2) passing the second liquid layer through solid ammonium sulfate for a time sufficient to agglomerate the discontinuous phase; and (3) separating the agglomerated discontinuous phase from the continuous phase.

The process is particularly applicable when the product is an oxime such as 2-methyl-2-methylthio-propionaldehyde oxime (Aldicarb oxime), cyclohexanone oxime or methylethylketoxime.

DETAILED DESCRIPTION OF THE INVENTION

The process of the present invention employs solid ammonium sulfate to agglomerate and remove the discontinuous phase from the continuous phase of an emulsion in which the continuous phase is the desired organic, substantially water-insoluble oxime product and the discontinuous phase is aqueous ammonium sulfate. As described in the background section above, such impure product emulsions are often found in the production of various oximes. The present invention is applicable only to oxime products which are "substantially water-insoluble" by which is meant having at most about 5 weight percent water soluble in the pure oxime at room temperature and preferably at most about 1 weight percent water soluble in the pure product at room temperature. It should be appreciated that the presence of salts such as ammonium sulfate in a discontinuous phase will lower the amount of water actually present in the continuous phase of the emulsion below the theoretical solubility of pure water in the organic product.

Exemplary suitable organic products include Aldicarb oxime, methylethylketoxime, cyclohexanone oxime, acetone oxime, n-butyraldehyde oxime and i-butyraldehyde oxime. The three first named products are preferred because of their commercial significance. Also preferred are organic, substrate water-insoluble products which are liquid at room temperature or at convenient operating temperatures. Thus the product has a preferred melting point below about 75° C., more preferably below about 20° C.

The liquid reaction mixture contains water, ammonium sulfate and oxime product, and may be limited to these materials. It may also contain other materials such as original reactants (ketones or aldehydes in the case of oximes), unneutralized acid such as sulfuric acid, free bases such as ammonia or ammonium hydroxide, by-products such as nitrites, unsaturates, bisulfates, methyl mercaptan, and ammonium chloride.

These materials will normally be separated from the oxime product by either the phase separation or by the subsequent distillation or distillations. They have no substantial effect on the present process.

The separation of the reaction mixture into the first and second liquid layers is conducted as a normal phase separation. Thus the reaction mixture may be fed to a conventional column, tank, or phase separator and the first layer and second layer withdrawn from the top and bottom, or vice versa depending upon their relative densities. On the laboratory scale this is easily accomplished with a separatory funnel. Ammonium sulfate may be crystallized from the first layer in conventional fashion.

The second layer (an emulsion) is then contacted with ammonium sulfate to agglomerate the discontinuous phase. It is preferred to use crystalline or unhydrated ammonium sulfate also called mascagnite and having the formula $(NH_4)_2SO_4$. Other forms of the material may be used such as ammonium bisulfate $(NH_4)HSO_4$. Since both forms are very soluble in water (about 100 g/L or higher) the term "solid ammonium sulfate" excludes the use of even very concentrated solution but does not exclude hydrated forms or slurries in which less water is present than is required to dissolve the salt. Preferably the ammonium sulfate used has at most about 5% water, more preferably at most about 1% water.

The contact time, temperature, mixing conditions and relative amounts of ammonium sulfate and second layer each are not independently critical. Together they must be adjusted to agglomerate the discontinuous phase into large (greater than about 0.5–1 mm) droplets. It is convenient to provide ammonium sulfate in excess as by passing the second layer through a bed of solid ammonium sulfate. Room temperature is preferred unless higher temperatures are required to melt the product, in which case temperatures sufficiently above the melting point to avoid product crystallizing or excessive viscosities should be employed. The contact time, as determined by granular size, bed dimensions and flow rate can be easily adjusted to achieve the desired effect.

The agglomeration is believed to be the result of two occurrences, first dissolving of ammonium sulfate into the discontinuous phase of the second layer and second adherence of small droplets to the solid ammonium sulfate particles where they can coalesce into larger droplets. The adherence and coalescense effect can be achieved with other solids such as nylon or other fibers such as fiberglass or cellulose. Coalescing agents of this type are sold, for example, by Selas Corporation of America and described in their Bulletin entitled "Coalescing of Liquids Through Porous Materials." Such coalescing agents are, however, incapable of increasing the salt concentration in the discontinuous phase. It is believed that by increasing the salt concentration several beneficial effects may occur: (1) the tendency of the discontinuous phase to agglomerate may increase, (2) water may be removed from the continuous phase, (3) the density of the discontinuous phase may increase facilitating later separation if the continuous phase is less dense and (4) separation conditions are more uniform with a saturated aqueous phase.

Once the contacting step is complete, the effluent may again be phase separated with the large droplets of discontinuous now separating clearly from the organic product. The aqueous phase may then be crystallized in conventional fashion. By using solid ammonium sulfate as the coalescing agent, the danger of introducing incompatible materials into the product is avoided. Furthermore, clogging of the bed of coalescing material can be avoided because the bed of ammonium sulfate dissolves away with use. It can be recharged continuously or periodically.

It has been found that the present process, when used in systems where the emulsion may contain over 50 ppm (0.005 weight percent) ammonium sulfate or even over 100 ppm (0.01 weight percent) ammonium sulfate, is effective to reduce the ammonium sulfate content to below about 25 ppm or even below about 10 ppm ammonium sulfate.

The separated product may then be purified by one or more distillations. Preferably it is first subjected to a lites distillation to remove low boilers and then to a product distillation to recover the product as an overhead. With certain stills these can be combined by taking the lites from the top of the still and the product from a somewhat lower point. In any event distillations have a tendency to concentrate the salt in the liquid phase. This effect is most significant when the product has a lower boiling point than water such that water is removed upon lites distillation. In such cases the bottoms from the lites column, especially if cooled by a heat exchanger or a similar device, is likely to become supersaturated in ammonium sulfate. The result is that ammonium sulfate will crystallize out, particularly on the heat exchanger surfaces, eventually impeding heat transfer and flow of liquid. In the commercial production of Aldicarb oxime this effect has forced periodic shutdowns to remove the ammonium sulfate as often as several times a week. By lowering the ammonium sulfate as much as tenfold, these shutdowns can either be avoided because the ammonium sulfate never becomes supersaturated or be slowed down to the point that continuous operation for days or even weeks is possible.

EXAMPLE 1—ALDICARB OXIME

A glass column, 2.9 cm (1⅛ inch) inside diameter was charged with 100 g of crystal ammonium sulfate and clamped vertically. A sample of crude 2-methyl-2-methylthio propionaldehyde oxime (Aldicarb oxime) appearing cloudy and containing 388 ppm ammonium sulfate was continuously fed at the top of the column, with a free liquid level of about 12 inches maintained at the top of the bed. The feed rate averaged 110 mL/h. After collection of between 150 and 200 mL of the liquid out of the bottom of the column (after about 100 minutes), the effluent was still clear, with clearly separated aqueous droplets about 1 mm in diameter settling in the bottom of the receiver. The fourth 100 mL of effluent was collected, and allowed to settle in a separatory funnel. The clear organic layer was decanted off and found to contain 14 ppm ammonium sulfate.

EXAMPLE 2—ALDICARB OXIME

Example 1 was repeated using a different crude Aldicarb oxime sample containing 85 ppm ammonium sulfate. A one foot head of liquid was maintained in the column and the flow rate was 110 mL/h. After liquid was flowing out of the column, a 100 mL sample was taken and allowed to settle in a separatory funnel. The organic layer was decanted off. The ammonium sulfate content of the decanted liquid was calculated as 6 ppm.

EXAMPLE 3—ALDICARB OXIME

Example 2 was repeated with the column first filled by crystalline ammonium sulfate, then by saturated aqueous ammonium sulfate and then by a continuous feed of emulsion. The results were substantially identical.

EXAMPLE 4—METHYLETHYL KETOXIME

The procedure of Example 1 was followed with methylethyl ketone containing 71 ppm ammonium sulfate. The effluent from the ammonium sulfate column consisted of a clear organic upper layer with essentially saturated ammonium sulfate solution droplets of about 1 mm diameter quickly separating to the bottom in a clear layer. The collected upper layer contained 16 ppm ammonium sulfate.

What is claimed is:

1. A process for recovering an organic, substantially water-insoluble oxime product from a liquid reaction mixture comprising water, ammonium sulfate and the product, which process comprises:
    (1) separating the reaction mixture into a first liquid layer comprising an aqueous ammonium sulfate solution and a second liquid layer comprising an emulsion of the organic oxime product as the continuous phase and aqueous ammonium sulfate as the discontinuous phase;

(2) passing the second liquid layer through solid ammonium sulfate for a time sufficient to agglomerate the discontinuous phase; and (3) separating the agglomerated discontinuous phase from the continuous phase.

2. The process of claim 1 wherein said oxime product is 2-methyl-2-methylthio-propionaldehyde oxime.

3. The process of claim 1 wherein said oxime product is cyclohexanone oxime.

4. The process of claim 1 wherein said oxime product is methylethylketoxime.

5. The process of claim 1 wherein said oxime product is distilled from said continuous phase.

6. The process of claim 1 wherein a lites fraction is distilled from said continuous phase.

7. The process of claim 1, claim 2, claim 3, or claim 4 wherein a lites fraction is distilled from said continuous phase and said oxime product is then distilled from said continuous phase.

* * * * *